US011583343B2

(12) United States Patent
Bendok et al.

(10) Patent No.: US 11,583,343 B2
(45) Date of Patent: Feb. 21, 2023

(54) 3D TRACKING-ASSISTED FUNCTIONAL BRAIN REGION MAPPING

(71) Applicant: Mayo Foundation for Medical Education and Research, Rochester, MN (US)

(72) Inventors: Bernard R. Bendok, Phoenix, AZ (US); Rami James N. Aoun, Phoenix, AZ (US); Barrett Anderies, Phoenix, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 665 days.

(21) Appl. No.: 16/608,099

(22) PCT Filed: Apr. 26, 2018

(86) PCT No.: PCT/US2018/029553
§ 371 (c)(1),
(2) Date: Oct. 24, 2019

(87) PCT Pub. No.: WO2018/200801
PCT Pub. Date: Nov. 1, 2018

(65) Prior Publication Data
US 2020/0093547 A1    Mar. 26, 2020

Related U.S. Application Data

(60) Provisional application No. 62/490,808, filed on Apr. 27, 2017.

(51) Int. Cl.
*A61B 34/00* (2016.01)
*A61B 34/20* (2016.01)
(Continued)

(52) U.S. Cl.
CPC .............. *A61B 34/20* (2016.02); *A61B 5/389* (2021.01); *A61B 34/76* (2016.02); *A61N 1/0531* (2013.01);
(Continued)

(58) Field of Classification Search
CPC ................ A61B 17/29; A61B 18/1442; A61B 2017/00119; A61B 2018/00446;
(Continued)

(56) References Cited

U.S. PATENT DOCUMENTS

| 6,381,485 B1 | 4/2002 | Hunter et al. |
| 7,072,707 B2 | 7/2006 | Galloway, Jr. et al. |

(Continued)

FOREIGN PATENT DOCUMENTS

| CA | 2 931 877 | 8/2016 |
| DE | 196 39 615 | 4/1998 |

(Continued)

OTHER PUBLICATIONS

Anderies et al., "3D Tracking-Assisted Functional Region Mapping Tool for Awake Neurosurgery," Poster, Presented at Arizona State University biomedical engineering capstone symposiumon Apr. 28, 2017, 1 page.

(Continued)

*Primary Examiner* — George Manuel
(74) *Attorney, Agent, or Firm* — Fish & Richardson P.C.

(57) ABSTRACT

Systems and methods are described for functional brain mapping using neuronavigational equipment and additional features. For example, some implementations described combine novel cortical stimulator tools with stereotactic navigation for three-dimensional position tracking of the cortical stimulator tools. In some implementations, the systems and methods described herein can be used on an awake patient. In some implementations, the systems and methods (Continued)

described herein can be used on a patient that is asleep, via motor evoked potentials (MEPs), phase reversal, or electromyography (EMG) monitoring. Accordingly, in some cases sensory and language regions of the brain can be identified in addition to motor regions.

21 Claims, 4 Drawing Sheets (51) Int. Cl.
| | |
|---|---|
| A61N 1/05 | (2006.01) |
| A61B 5/389 | (2021.01) |
| A61B 34/10 | (2016.01) |
| A61B 90/00 | (2016.01) |
| A61B 17/29 | (2006.01) |
| A61B 17/00 | (2006.01) |
| A61B 18/00 | (2006.01) |

(52) U.S. Cl.
CPC ..... *A61B 17/29* (2013.01); *A61B 2017/00119* (2013.01); *A61B 2018/00595* (2013.01); *A61B 2034/105* (2016.02); *A61B 2034/107* (2016.02); *A61B 2090/397* (2016.02); *A61B 2217/005* (2013.01); *A61B 2505/05* (2013.01)

(58) Field of Classification Search
CPC .... A61B 2018/00595; A61B 2018/126; A61B 2034/105; A61B 2034/107; A61B 2034/2051; A61B 2034/2055; A61B 2090/397; A61B 2090/3983; A61B 2217/005; A61B 2505/05; A61B 34/20; A61B 34/76; A61B 5/389; A61B 90/90; A61N 1/0456; A61N 1/0472; A61N 1/05; A61N 1/0531; A61N 1/36; A61N 1/36014
See application file for complete search history.

(56) References Cited

U.S. PATENT DOCUMENTS

| | | | |
|---|---|---|---|
| 7,558,617 B2 | 7/2009 | Vilsmeier | |
| 7,647,087 B2 | 1/2010 | Miga et al. | |
| 8,116,848 B2 | 2/2012 | Shahidi | |
| 8,463,360 B2 | 6/2013 | Yamamoto et al. | |
| 8,548,565 B2 | 10/2013 | Hunter et al. | |
| 8,660,635 B2 | 2/2014 | Simon et al. | |
| 8,761,869 B2 | 6/2014 | Leuthardt et al. | |
| 9,119,670 B2 | 9/2015 | Yang et al. | |
| 9,226,800 B2 | 1/2016 | Burg et al. | |
| 2001/0029333 A1 | 10/2001 | Shahidi | |
| 2002/0095081 A1 | 7/2002 | Vilsmeier | |
| 2003/0000535 A1 | 1/2003 | Galloway, Jr. et al. | |
| 2004/0131998 A1* | 7/2004 | Marom | A61N 1/3603 607/45 |
| 2006/0100526 A1 | 5/2006 | Yamamoto et al. | |
| 2008/0183068 A1 | 7/2008 | Carls et al. | |
| 2010/0298907 A1 | 11/2010 | Lombardi et al. | |
| 2015/0351860 A1 | 12/2015 | Piron et al. | |
| 2016/0346544 A1 | 12/2016 | Byrne | |
| 2020/0093547 A1 | 3/2020 | Bendok | |

FOREIGN PATENT DOCUMENTS

| | | |
|---|---|---|
| EP | 2967292 | 1/2016 |
| WO | WO 2005/025404 | 3/2005 |
| WO | WO 2015/149854 | 10/2015 |
| WO | WO 2016/007553 | 1/2016 |
| WO | WO 2016/172370 | 10/2016 |
| WO | WO 2017/033040 | 3/2017 |
| WO | WO 2017/060755 | 4/2017 |

OTHER PUBLICATIONS

Bello et al., "Motor and language DTI Fiber Tracking combined with intraoperative subcortical mapping for surgical removal of gliomas," Neuroimage, 39(1):369-82, Jan. 2008.
Berman et al., "Diffusion-tensor imaging-guided tracking of fibers of the pyramidal tract combined with intraoperative cortical stimulation mapping in patients with gliomas," Journal of neurosurgery, 101(1):66-72, Jul. 2004.
Bunyaratavej et al., "Continuous physical examination during subcortical resection in awake craniotomy patients: Its usefulness and surgical outcome," Clinical neurology and neurosurgery, 147:34-8, Aug. 2016.
Elhawary et al., "Intraoperative real-time querying of white matter tracts during frameless stereotactic neuronavigation," Neurosurgery, 68(2):506-16, Feb. 2011.
Gamble et al., "Awake craniotomy in arteriovenous malformation surgery: the usefulness of cortical and subcortical mapping of language function in selected patients," World neurosurgery, 84(5):1394-401, Nov. 2015.
Garrett et al., "Use of language mapping to aid in resection of gliomas in eloquent brain regions," Neurosurgery Clinics, 23(3):497-506, Jul. 2012.
International Preliminary Report on Patentability in International Application No. PCT/US2018/029553 dated Nov. 7, 2019, 17 pages.
International Search Report & Written Opinion in International Application No. PCT/US2018/029553 dated Jul. 27, 2018, 33 pages.
Ojemann et al., "Cortical language localization in left, dominant hemisphere: an electrical stimulation mapping investigation in 117 patients," Journal of neurosurgery, 71(3):316-326, Sep. 1989.
Spena et al., "Purely subcortical tumors in eloquent areas: awake surgery and cortical and subcortical electrical stimulation (CSES) ensure safe and effective surgery," Clinical neurology and neurosurgery, 115(9):1595-601, Sep. 2013.
Szelényi et al., "Intraoperative electrical stimulation in awake craniotomy: methodological aspects of current practice," Neurosurgical focus, 28(2):E7, Feb. 2010.
Yamaguchi et al., "Navigation-assisted subcortical mapping: intraoperative motor tract detection by bipolar needle electrode in combination with neuronavigation system," Journal of neuro-oncology, 93(1):121, May 2009.

* cited by examiner

3D TRACKING-ASSISTED FUNCTIONAL BRAIN REGION MAPPING

CROSS-REFERENCE TO RELATED APPLICATIONS

This application is a National Stage application under 35 U.S.C. § 371 of International Application No. PCT/US2018/029553, having an International Filing Date of Apr. 26, 2018, which claims the benefit of U.S. Provisional Application Ser. No. 62/490,808, filed Apr. 27, 2017. The disclosures of the prior applications are considered part of (and are incorporated by reference in) the disclosure of this application.

BACKGROUND

1. Technical Field

This document relates to systems and methods for functional brain mapping. For example, this document relates to functional brain mapping systems that incorporate a cortical simulator tool along with stereotactic navigation for three-dimensional position tracking of the cortical stimulator tools.

2. Background Information

During certain neurosurgical procedures, surgeons endeavor to precisely localize critical brain regions, such as those that control motor, vision, and language functions to avoid damaging these areas. However, even with extensive knowledge of brain anatomy and preoperative imaging, it is not possible to know for certain beforehand exactly what regions will be motor or fluent, for example. While diffusion tensor imaging (DTI) and functional magnetic resonance imaging (fMRI) can be used to estimate the locations of white matter tracts and region functions, respectively, the function of a given region cannot be known for certain preoperatively. Furthermore, the brain can shift when a patient's head is positioned differently on the operating table than when they were in the imaging instrument, and loss of cerebrospinal fluid (CSF) during surgery can cause the brain to sag. Together, anatomical variation and brain shift reduce confidence in medical imaging accuracy and functional region location during surgery.

Currently, intraoperative brain mapping (e.g., awake neurosurgery) is often utilized to map functional regions. This technique generally involves electrical interrogation of cortex and white matter tracts, observing patient response to stimulus, and physically marking identified regions with sterile paper tags. The paper tags serve as a visual reminder to the surgeon later in the procedure.

SUMMARY

This document describes systems and methods for functional brain mapping using neuronavigational equipment and additional features. For example, some implementations described herein combine a novel cortical simulator with stereotactic navigation. In some implementations, the systems and methods described herein can be used on an awake patient. In some implementations, the systems and methods described herein can be used on a patient that is asleep, via motor evoked potentials (MEPs), phase reversal, or electromyography (EMG) monitoring. Accordingly, vision and language functional areas can be identified, in addition to motor function areas.

In one aspect, this disclosure is directed to a cortical stimulator device. The cortical stimulator device includes a main body having a proximal end portion and a distal end portion, a plurality of infrared (IR) reflective spheres attached to the proximal end portion of the main body, and bipolar cortical stimulator electrodes attached to the distal end portion of the main body.

Such a cortical stimulator device may optionally include one or more of the following features. The cortical stimulator device may also include a mapping actuation input device coupled to the main body. The mapping actuation input device may be configured to be actuated by a user of the cortical stimulator device to tag a location on a patient's brain. The cortical stimulator device may also include a switch for activating energy delivery from the bipolar cortical stimulator electrodes. The cortical stimulator device may also include a haptic feedback device coupled to the main body.

In another aspect, this disclosure is directed to a cortical stimulator device. The cortical stimulator device includes a main body having a proximal end portion and a distal end portion, a plurality of infrared (IR) reflective spheres attached to the proximal end portion of the main body, and a monopolar cortical stimulator electrode attached to the distal end portion of the main body.

Such a cortical stimulator device may optionally include one or more of the following features. The cortical stimulator device may also include a mapping actuation input device coupled to the main body. The mapping actuation input device may be configured to be actuated by a user of the cortical stimulator device to tag a location on a patient's brain. The cortical stimulator device may also include a switch for activating energy delivery from the monopolar cortical stimulator electrode. The cortical stimulator device may also include a haptic feedback device coupled to the main body.

In another aspect, this disclosure is directed to a surgical system including a cortical stimulator device and a 3D tracking system. The cortical stimulator device includes a main body having a proximal end portion and a distal end portion, a plurality of IR reflective spheres attached to the proximal end portion of the main body, and bipolar cortical stimulator electrodes (or a monopolar cortical stimulator electrode) attached to the distal end portion of the main body. The 3D tracking system is configured to track the plurality of IR reflective spheres so that a location of the bipolar cortical stimulator electrodes (or the monopolar cortical stimulator electrode) can be determined by the 3D tracking system.

Such a surgical system may optionally include one or more of the following features. The surgical system may also include a surgical tool including a plurality of IR reflective spheres attached to a proximal end of the surgical tool. The surgical tool may be a cautery tool. The surgical tool may be forceps. The surgical tool may be a suction device. The surgical system may also include a mapping actuation input device coupled to the main body of the cortical stimulator device. The mapping actuation input device may be configured to be actuated by a user of the cortical stimulator device to tag a location on a patient's brain. In some implementations, an actuation of the mapping actuation input device sends a signal to the 3D tracking system, and causes the 3D tracking system to register the tagged location on the patient's brain. The 3D tracking system may be configured to output an alert message when a surgical tool is detected by the 3D tracking system as being within a threshold distance from the tagged location on the patient's brain. In some embodiments, the 3D tracking system may be configured to output an alert message when a surgical tool is detected by the 3D tracking system as meeting positional criteria relative to a tagged 3D region relative to the patient's brain. Any type of 3D area shape, as desired, can be established using, the stimulator probe as a "3D paintbrush" or in software, for example.

In another aspect, this disclosure is directed to a method of using a surgical system. The method includes stimulating, using a cortical stimulator device, an area on a surface of a patient's brain, in response to receiving a patient response to the stimulating, actuating a mapping actuation input device on the main body of the cortical stimulator device to identify a tagged location on a patient's brain, and in response to the actuating, registering, using a 3D tracking system that views the plurality of IR reflective spheres, the tagged location on the patient's brain in a memory of the 3D tracking system. The cortical stimulator device includes a main body having a proximal end portion and a distal end portion, a plurality of IR reflective spheres attached to the proximal end portion of the main body, and bipolar cortical stimulator electrodes (or a monopolar cortical stimulator electrode) attached to the distal end portion of the main body.

Such a method of using a surgical system may optionally include one or more of the following features. The method of may also include tracking, by the 3D tracking system, a location of a tip of a surgical tool being used to operate on the patient's brain. The method may also include comparing, by the 3D tracking system, the location of the tip of the surgical tool to the tagged location on a patient's brain. The method may also include providing an alert, by the 3D tracking system, when it is determined, using the comparing step, that the location of the tip of the surgical tool is within a threshold distance from the tagged location on a patient's brain. In some embodiments, the stimulating is performed while the patient is awake.

Particular embodiments of the subject matter described in this document can be implemented to realize one or more of the following advantages. For example, the combination of a cortical simulator with stereotactic navigation advantageously allows stimulation of brain tissue and creation of three-dimensional digital location tags (which can be used instead of the paper tags in some cases). The systems also provide alerts and/or alarms about tool position to the operating surgeon, allowing the surgeon to operate without looking away from the surgical area while maintaining awareness of the location of critical areas. Additionally, as described further below, the capability of the systems and methods provided herein to localize sensory and language regions of the patient's brain is an advantage of the systems and methods provided herein.

Some systems described herein advantageously provide sub-millimeter accuracy for tools less than 200 mm (which is typical for most surgical tools used in this surgical context). Moreover, devices described herein are advantageously compatible with existing neuronavigational systems. Therefore, the devices can be used as a stand-alone system or as an add-on for existing stereotactic systems.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes systems and methods for functional brain mapping using neuronavigational equipment and additional features. For example, some implementations described herein combine novel cortical stimulator tools with stereotactic navigation for three-dimensional (3D) position tracking of the cortical stimulator tools.

In some implementations, the systems and methods described herein can be used on an awake patient. This way, the systems and methods provided herein can be used to localize the patient's brain regions including: motor, sensory (which relies on the patient reporting a sensation, and would not be available from motor evoked potentials (MEPs)), and language (which requires the patient to be speaking during stimulation). Accordingly, the systems and methods described herein need not rely solely on MEPs, but rather can utilize interactions with the patient during stimulation. The capability to localize sensory and language regions of the patient's brain is an advantage of the systems and methods provided herein. Altogether, the systems and methods described herein will improve efficacy and safety of neurosurgery near motor and fluent regions.

In some implementations, the systems and methods described herein can be used in conjunction with other monitoring methods such as, but not limited to, MEPs, phase reversal, and EMG. In some cases, the method of monitoring patient response to stimulus can be selected depending on the region being mapped. For certain regions (at the surgeon's discretion), the surgery can be done with the patient asleep using monitoring modalities monitoring methods such as, but not limited to, MEPs, phase reversal, and EMG.

It should be understood that the systems and methods described herein are applicable for use with any brain mapping procedure, asleep and awake.

The systems and methods described herein can be used in contexts such as, but not limited to, resections for epilepsy, brain tumor resections (e.g., gliomas), and neurovascular procedures.

In some implementations, the cortical stimulator devices described herein are used to apply stimulatory current to cortex/white brain matter. Additionally, in some implementations the systems described herein can be operated to create digital location tags based on the cortical stimulator's tip location (which is tracked by a 3D tracking system). Such digital location tags can be visualized on medical imaging systems in 2D and/or 3D. Moreover, in some implementations, the systems described herein include an integrated surgical navigation and guidance system which alerts surgeons in real-time (e.g., via haptic or audiovisual feedback) when surgical instruments used by the surgeon (and tracked by the 3D tracking system) are positioned close to those tagged regions.

The systems described herein can use IR 3D tracking systems to estimate tool position in 3D space. Such IR 3D tracking systems can include, but are not limited to systems such as the NDI POLARIS VICRA®, NDI POLARIS SPECTRA®, or NDI POLARIS VEGA® (from Northern Digital Inc.), or tracking systems from other manufacturers. Such systems allow the position of the tip the cortical stimulator tools and other surgical tools, which will be in contact with brain tissue, to be monitored in real time. When a button on the cortical stimulator tool is pressed, the tool tip location will be used to create a 3D digital location tag with information regarding the position, warning radius, and any other pertinent information. Alternatively, or additionally, the systems described herein can use electromagnetic tracking systems to estimate tool position in 3D space. In some such cases, the IR reflective tracking spheres on the cortical stimulator tools and other surgical tools are replaced by, or supplemented by, one or more electromagnetic field locators.

In some implementations, the physical cortical stimulator tool itself is a bipolar stimulator with a bayoneted tip to maximize visibility of the operating area. Alternatively, a monopolar simulator electrode can be used. In addition to electrodes to deliver stimulatory current to the interrogated regions, the cortical stimulator tool can optionally contain a momentary switch to trigger tagging and/or an actuator to provide haptic feedback (such as a linear resonant actuator or other appropriate haptic feedback device). In some embodiments, the cortical stimulator tool has IR reflective spheres on the rear end to allow 3D tracking by the tracking camera. In some embodiments, the IR reflective tracking spheres on the cortical stimulator tool (and/or other surgical tools described herein) are replaced by, or supplemented by, one or more electromagnetic field locators (e.g., EM emitter(s)) when an EM tracking system is used as part of the systems described herein.

The proposed digital method of functional brain region mapping has the advantage of potentially being seamlessly integrated with existing 3D tracking systems, and will not suffer from some of the drawbacks of the current method of functional region mapping. As a digital system, it is possible to integrate the system with more standard surgical tools to provide real-time haptic feedback to alert the user when he or she is encroaching on a brain region that has been tagged, e.g., as motor or fluent. For example, the system described herein can include IR reflective spheres attachments for a surgical suction and bipolar forceps (when IR tracking is employed, or an EM emitter when an EM tracking system is employed), allowing these tools to be tracked during surgery in addition to the custom stimulatory and tagging tool.

The attachments to the surgical tools include the IR reflective spheres and, optionally, a device (e.g., a linear resonant actuator) to provide haptic feedback if and when the tool enters a region that has been tagged using the stimulator/tagging tool. This allows the user to receive pertinent information about tagged areas of the brain without having to look away from the surgical area (via any combination of auditory, visual or haptic feedback). Additionally, all of the tag information can be overlaid on the 2D and 3D patient scans, allowing all tags to be viewed on a monitor as they relate to the anatomy visible in the preoperative scan and 3D reconstruction. Overall, the digital integration of a previously purely physically based method provides more continuous and integrated workflow, and allows for a software and hardware platform for future development of novel surgical tools and related device innovations.

Figure 1:
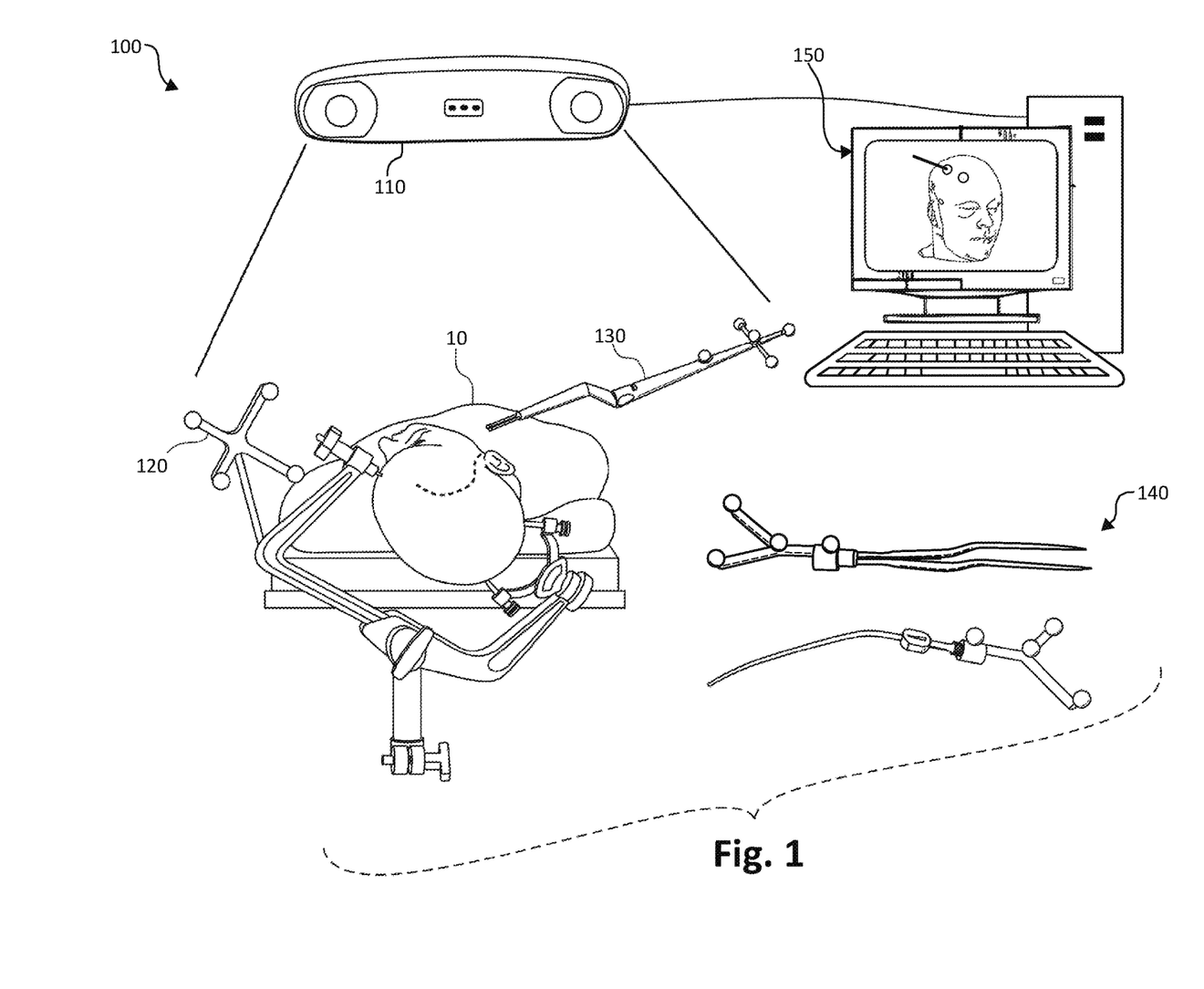
FIG. 1 is a schematic diagram of patient undergoing a brain surgery using the systems and methods for functional brain mapping as described herein.

Referring to FIG. 1, an example system 100 for performing a brain surgery on a head-fixed patient 10 can include an IR 3D tracking system 110 (or an EM tracking system), a patient registration device 120, a positionally-trackable cortical stimulator tool 130, additional positionally-trackable surgical tools 140, and a surgical navigation and mapping system 150. System 100 allows for functional brain mapping and three-dimensional position tracking of surgical tools so that important regions of the brain can be avoided. In some implementations, system 100 (e.g., the use of cortical stimulator tool 130) can be used while patient 10 is awake. Accordingly, in some cases sensory and language regions of the brain can be identified, in addition to motor regions.

3D tracking system 110 in conjunction with surgical navigation and mapping system 150 can locate and track the position of patient 10 and of devices such as cortical stimulator tool 130 and other positionally-trackable surgical tools 140. For example, patient registration device 120 (which is fixed in relation to the skull of patient 10) includes an arrangement of IR reflective spheres that are detectable by 3D tracking system 110 so as to indicate the position and orientation of patient 10. The patient positional information detected by 3D tracking system 110 is provided to surgical navigation and mapping system 150 for storage, computations, display, and so on.

3D tracking system 110 in conjunction with surgical navigation and mapping system 150 can also locate and track the position of cortical stimulator tool 130. Accordingly, stimulation and mapping of the locations of functional regions of the patient's brain can be performed using system 100, as described further herein. The mapping technique can result in the creation of 3D digital location tags or tagged areas/regions (which can be used instead of the paper tags in some cases) stored by surgical navigation and mapping system 150.

Optionally, 3D tracking system 110 in conjunction with surgical navigation and mapping system 150 can also locate and track the position of other positionally-trackable surgical tools 140. Using that functionality, surgical navigation and mapping system 150 can provide alerts and/or alarms when positionally-trackable surgical tools 140 get positioned within a threshold distance from a tagged area of the patient's brain. This provides information about tool position to the operating surgeon, while allowing the surgeon to operate without looking away from the surgical area and maintaining awareness of the location of critical areas of the brain.

Figure 2:
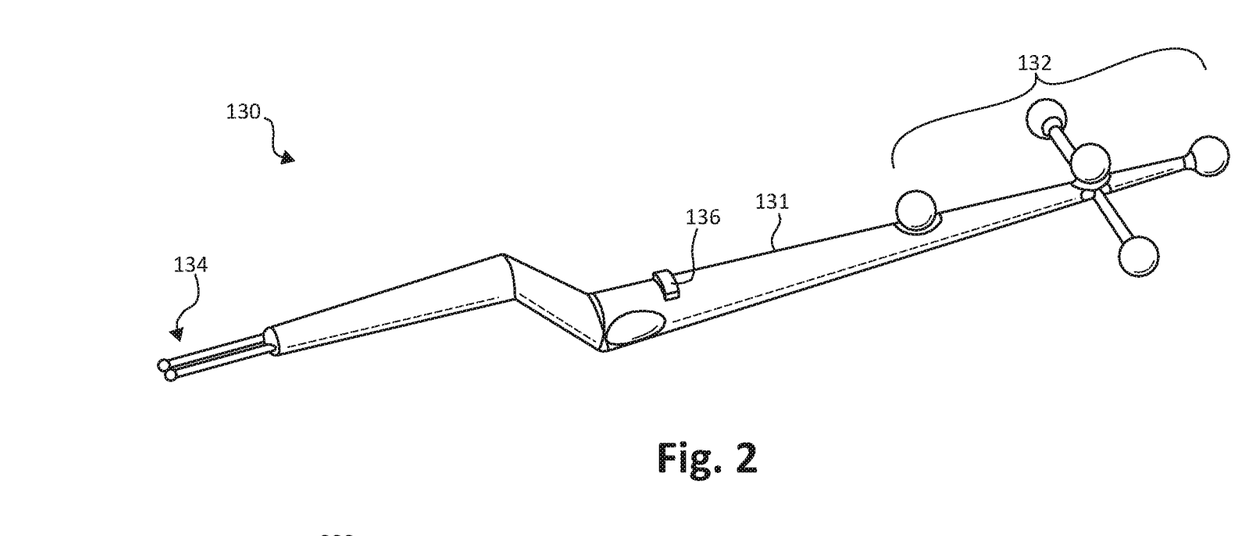
FIG. 2 is a perspective view of an example positionally-trackable cortical stimulator tool in accordance with some embodiments provided herein.

Referring to FIG. 2, example cortical stimulator tool 130 can be seen in more detail. Cortical stimulator tool 130 includes a main body 131, a plurality of IR reflective spheres 132 located at a proximal end portion of main body 131, and bipolar cortical stimulator electrodes 134 are located at a distal end of main body 131. In some embodiments, a monopolar cortical stimulator electrode can be used rather than the bipolar cortical stimulator electrodes 134. In a novel manner, cortical stimulator tool 130 combines two or more technologies, i.e., electrodes 134 to deliver electrical stimulation to brain tissue, and IR reflective spheres 132 to enable 3D tracking.

In some implementations, the delivery of stimulation energy is activated by the use of a foot pedal input device, for example. Alternatively, or additionally, in some implementations an input device can be located on cortical stimulator tool 130 such that the delivery of stimulation energy can be activated by actuating an input device (e.g., switch) directly coupled to cortical stimulator tool 130.

In some implementations, cortical stimulator tool 130 includes a mapping actuation input device 136. Mapping actuation input device 136 can be manually triggered by the user of cortical stimulator tool 130 (e.g., surgeon) when it is desired to map a particular location where the bipolar cortical stimulator electrodes 134 are positioned. This could be used, for example, in response to identifying a motor, sensory, and/or language functional region of the patient's brain that is to be avoided during a subsequent surgical procedure (e.g., resections for epilepsy, brain tumor resections (e.g., gliomas), and neurovascular procedures). In some implementations, other mapping actuation input devices can be used such as, but not limited to, voice input, foot pedal, and the like. In some implementations, cortical stimulator tool 130 can be used to map a 3D region to be subsequently avoided using a "paintbrush" feature. Accordingly, a 3D region of any shape and size can be marked, drawn, or otherwise created using cortical stimulator tool 130.

In some implementations, cortical stimulator tool 130 includes and optional haptic feedback device (not shown). Such a haptic feedback device can be used to provide an alert/alarm to the surgeon when cortical stimulator tool 130 is within a threshold distance of a previously mapped/tagged location of the brain. Additionally, or alternatively, in some implementations other types of feedback can be provided when cortical stimulator tool 130 is within a threshold distance of a previously mapped/tagged location of the brain. The feedback can include, but is not limited to, audible tones, visual indicators, and the like. In some implementations, the intensity of the feedback can be provided in proportion to the distance away from the previously mapped/tagged location of the brain.

Additionally, specific information about the anatomical region can be added to the saved tag location, including determined function ("hand motor," "hand sensory," "language," etc.), the radius of warning, tag color on the surgical monitor(s), and any other notes desired. Once tagging of functional regions is complete, the operating surgeon will switch to more typical surgical tools, such as the suction and bipolar forceps described below. These surgical tools will include attachments that allow them to be tracked. If at any time the tip of the surgical tool(s) is/are located within a certain distance (the radius of warning, or threshold distance of warning) of a tagged region/area, the system will alert the surgeon to this encroachment. This warning can be any combination of auditory, haptic or visual feedback, depending on preference. Auditory feedback includes a tone, multiple tones, or verbal warnings (the system will say "hand motor," for example). Proximity to the tag can be communicated by volume level or frequency of alerts (the system will repeat the warning at a faster rate as the tool moves closer to the tag location, for example). At any point, the operating surgeon can move the tracked tool(s) to visualize different slices (sagittal, coronal, transverse) of the patient scans and digital tags on the surgical monitor(s).

Figure 3:
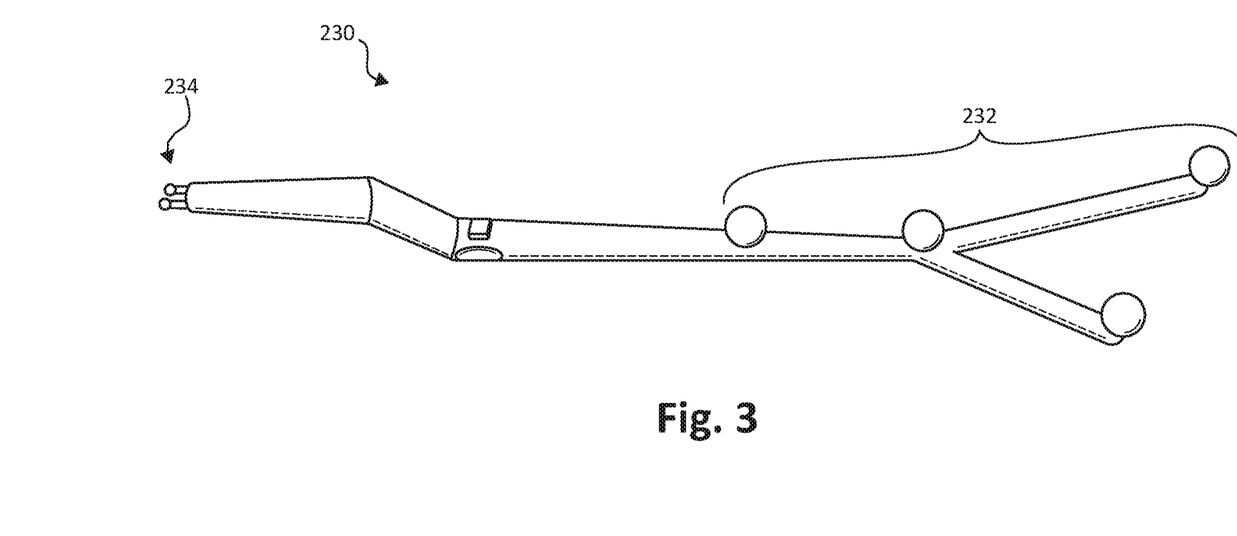
FIG. 3 is a perspective view of another example positionally-trackable cortical stimulator tool in accordance with some embodiments provided herein.

Referring to FIG. 3, another example cortical stimulator tool 230 is shown. Cortical stimulator tool 230 includes a plurality of IR reflective spheres 232 located at a proximal end portion of cortical stimulator tool 230. At a distal end of cortical stimulator tool 230, the bipolar cortical stimulator electrodes 234 are located. In some embodiments, a monopolar cortical stimulator electrode can be used rather than the bipolar cortical stimulator electrodes 234. In a novel manner, cortical stimulator tool 230 combines two or more technologies: electrodes 234 to deliver electrical stimulation to brain tissue, and IR reflective spheres 232 to enable 3D tracking.

In the depicted implementation, the four IR reflective spheres 232 of cortical stimulator tool 230 are all located in a common plane. Two spheres of IR reflective spheres 232 are located along the linear shaft of cortical stimulator tool 230. The other two spheres of IR reflective spheres 232 are located at respective the distal end portions of two bifurcated arms at the proximal end of cortical stimulator tool 230. One of the bifurcated arms is longer than the other bifurcated arm. Therefore, in the depicted non-limiting example arrangement, the respective IR spheres on the bifurcated arms are located at different distances and angles from the tip of bipolar cortical stimulator electrodes 234 (in accordance with techniques for IR tracking). It should be understood that such an arrangement of the IR reflective spheres 232 of cortical stimulator tool 230 is not required in all envisioned embodiments. The placement of IR reflective spheres is arbitrary apart from a single unique spacing requirement and having a minimum of three.

Cortical stimulator tool 230 can also include any of the devices and functionalities of cortical stimulator tool 130 described above.

Figure 4:
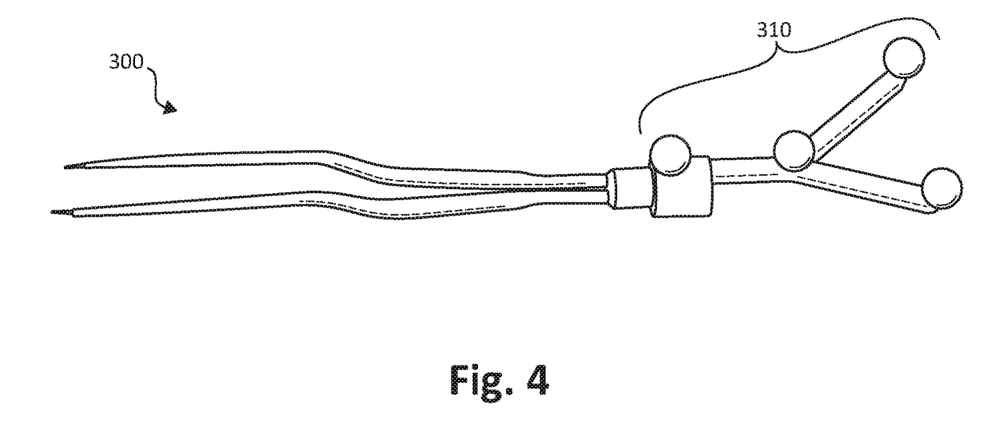
FIG. 4 is a perspective view of an example positionally-trackable bi-polar cautery forceps tool in accordance with some embodiments provided herein.

Referring to FIG. 4, various other surgical tools, such as the depicted positionally-trackable bi-polar cautery forceps tool 300, can also be used with the systems and methods described herein. Example bi-polar cautery forceps tool 300 includes a plurality of IR reflective spheres 310 at a proximal end of bi-polar cautery forceps tool 300. The four individual spheres of IR reflective spheres 310 are positioned in a manner similar to but dimensionally different from, the four IR reflective spheres 232 of cortical stimulator tool 230 as described above.

Optionally, positionally-trackable bi-polar cautery forceps tool 300 may include a haptic feedback device to provide an alert/alarm to the surgeon when bi-polar cautery forceps tool 300 is within a threshold distance of a previously mapped/tagged location of the brain.

Figure 5:
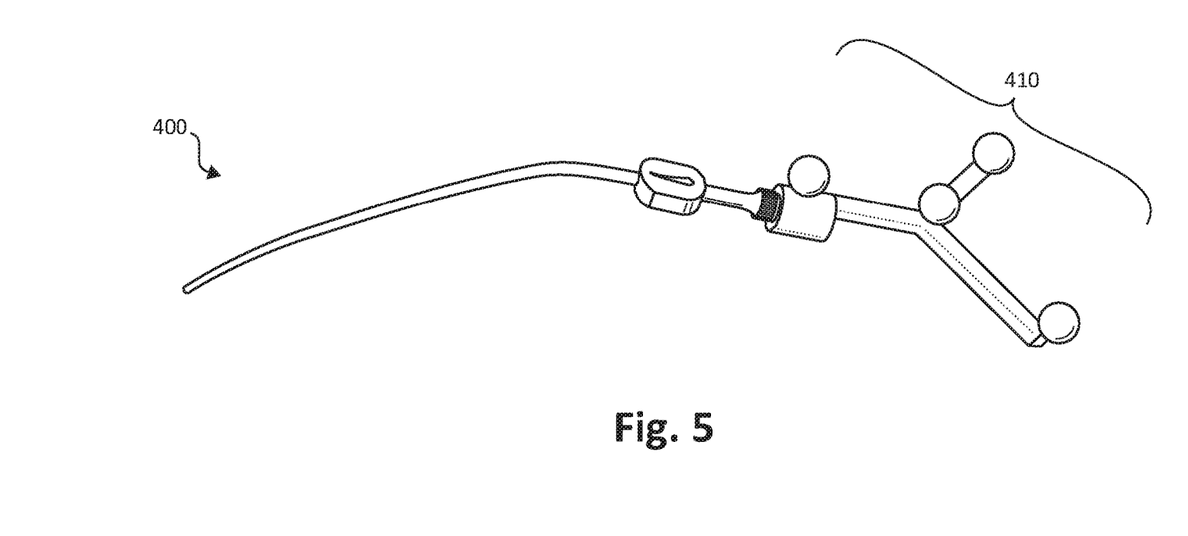
FIG. 5 is a perspective view of an example positionally-trackable suction tool in accordance with some embodiments provided herein.

Referring to FIG. 5, an example positionally-trackable suction tool 400 is shown. Suction tool 400 includes a plurality of IR reflective spheres 410 at a proximal end of suction tool 400. The four individual spheres of IR reflective spheres 410 are positioned in a manner similar to but dimensionally different from, the four IR reflective spheres 232 of cortical stimulator tool 230 as described above.

Optionally, positionally-trackable suction tool 400 may include a haptic feedback device to provide an alert/alarm to the surgeon when suction tool 400 is within a threshold distance of a previously mapped/tagged location of the brain.

It should be understood that other surgical tools can be equipped with a plurality of IR reflective spheres to make them trackable and thereby integrate-able with the systems and methods described herein.

Figure 6:
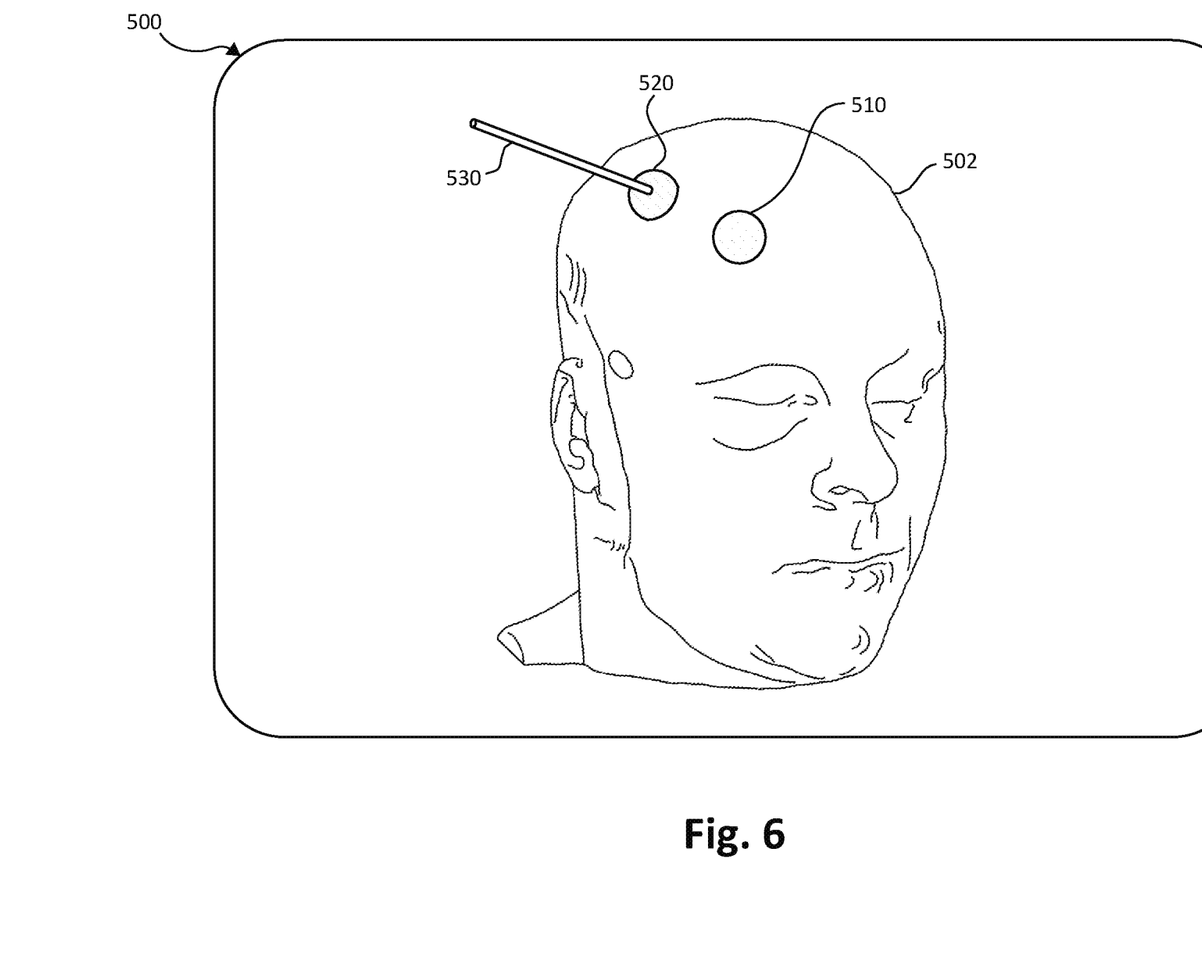
FIG. 6 is a simulated video screen showing locations of a patient's brain that have been tagged using the systems and methods provided herein.

FIG. 6 shows a screen 500 with a 3D reconstruction of a DICOM (digital imaging and communications in medicine) series of a patient's head 502, with custom tags applied. The display of this example visual image, and the functionality associated therewith, can be included as part of a surgical navigation and mapping system (e.g., surgical navigation and mapping system 150 described above in reference to FIG. 1), for example. In the depicted example, a first digitally-tagged location 510 and a second digitally-tagged location 520 are shown in relation to head 502. In some implementations, 3D regions on or relative to head 502 (or relative to the brain) can be digitally-tagged or created using a "paintbrush" technique. Such 3D regions can be a standard selected shape, or can be an arbitrary shape that is created by the process of digitally-tagging multiple locations.

These digitally-tagged locations 510 and 520 (and others as desired) can be established using the technique described above that employs a 3D-trackable cortical stimulator tool. In the depicted example, first digitally-tagged location 510 may be the location of a motor functional area and the second digitally-tagged location 520 may be the location of a sensory functional area, for example.

Screen 500 also depicts a simulated surgical tool 530. Simulated surgical tool 530 may correspond to a 3D-tracked surgical tool being used in real-time (e.g., positionally-trackable bi-polar cautery forceps tool 300 or positionally-trackable suction tool 400, as described above). In the illustrated example, simulated surgical tool 530 is encroaching on second digitally-tagged location 520. Therefore, second digitally-tagged location 520 is illustrated so as to indicate a warning (e.g., using a color change such as green to red, flashing, etc.). In addition, other alert/alarms can be issued, such as haptic, auditory, and/or visual alarms. Accordingly, the surgeon is notified that the tip of the surgical tool is in an area that should generally be avoided.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A cortical stimulator device, comprising:
    a main body having a proximal end portion and a distal end portion;
    a mapping actuation input device on the main body, the mapping actuation input device configured to be actuated by a user of the cortical stimulator device to tag a location on a patient's brain;
    a plurality of IR reflective spheres attached to the proximal end portion of the main body; and
    bipolar cortical stimulator electrodes attached to the distal end portion of the main body.

2. The cortical stimulator device of claim 1, further comprising a switch on the main body for activating energy delivery from the bipolar cortical stimulator electrodes.

3. The cortical stimulator device of claim 1, further comprising a haptic feedback device coupled to the main body.

4. A surgical system comprising:
    a cortical stimulator device comprising:
        a main body having a proximal end portion and a distal end portion;
        a mapping actuation input device on the main body, the mapping actuation input device configured to be actuated by a user of the cortical stimulator device to tag a location on a patient's brain;
        a plurality of IR reflective spheres attached to the proximal end portion of the main body; and
        bipolar cortical stimulator electrodes attached to the distal end portion of the main body; and
    a 3D tracking system configured to track the plurality of IR reflective spheres so that a location of the bipolar cortical stimulator electrodes can be determined by the 3D tracking system.

5. The surgical system of claim 4, further comprising a surgical tool including a plurality of IR reflective spheres attached to a proximal end of the surgical tool.

6. The surgical system of claim 5, wherein the surgical tool is a cautery tool.

7. The surgical system of claim 5, wherein the surgical tool is a forceps.

8. The surgical system of claim 5, wherein the surgical tool is a suction device.

9. The surgical system of claim 4, wherein an actuation of the mapping actuation input device sends a signal to the 3D tracking system, and causes the 3D tracking system to register the tagged location on the patient's brain.

10. The surgical system of claim 9, wherein the 3D tracking system is configured to output an alert message when a surgical tool is detected by the 3D tracking system as being within a threshold distance from the tagged location on the patient's brain.

11. The surgical system of claim 4, wherein an actuation of the mapping actuation input device sends a signal to the 3D tracking system, and causes the 3D tracking system to register a tagged 3D region of the patient's brain.

12. The surgical system of claim 11, wherein the 3D tracking system is configured to output an alert message when a surgical tool is detected by the 3D tracking system as meeting positional criteria in relation to the tagged 3D region of the patient's brain.

13. The surgical system of claim 4, wherein the cortical stimulator device further comprises a switch on the main body for activating energy delivery from the bipolar cortical stimulator electrodes.

14. A method of using a surgical system, the method comprising:
- stimulating, using a cortical stimulator device, an area on a surface of a patient's brain, the cortical stimulator device comprising:
  - a main body having a proximal end portion and a distal end portion;
  - a mapping actuation input device on the main body, the mapping actuation input device configured to be actuated by a user of the cortical stimulator device to tag a location on a patient's brain;
  - a plurality of IR reflective spheres attached to the proximal end portion of the main body; and
  - bipolar cortical stimulator electrodes attached to the distal end portion of the main body;
- in response to receiving a patient response to the stimulating, actuating the mapping actuation input device on the main body of the cortical stimulator device to identify a tagged location or tagged 3D region on a patient's brain; and
- in response to the actuating, registering, using a 3D tracking system that views the plurality of IR reflective spheres, the tagged location on the patient's brain in a memory of the 3D tracking system.

15. The method of claim 14, further comprising:
tracking, by the 3D tracking system, a location of a tip of a surgical tool being used to operate on the patient's brain.

16. The method of claim 15, further comprising:
comparing, by the 3D tracking system, the location of the tip of the surgical tool to the tagged location on the patient's brain.

17. The method of claim 16, further comprising:
providing an alert, by the 3D tracking system, when it is determined, using the comparing step, that the location of the tip of the surgical tool is within a threshold distance from the tagged location on the patient's brain.

18. The method of claim 15, further comprising:
comparing, by the 3D tracking system, the location of the tip of the surgical tool to the tagged 3D region on the patient's brain; and
providing an alert, by the 3D tracking system, when it is determined, using the comparing step, that the location of the tip of the surgical tool meets positional criteria relative to the tagged 3D region on the patient's brain.

19. The method of claim 14, wherein the stimulating is performed while the patient is awake.

20. The method of claim 14, wherein the patient response to the stimulating comprises monitoring one or more of electromyography, phase reversal monitoring, and motor evoked potentials.

21. The method of claim 14, wherein the cortical stimulator device further comprises a switch on the main body for activating energy delivery from the bipolar cortical stimulator electrodes.

* * * * *